US010869595B2

(12) United States Patent
Inoue

(10) Patent No.: US 10,869,595 B2
(45) Date of Patent: Dec. 22, 2020

(54) ENDOSCOPE SYSTEM, CONTROLLER, AND COMPUTER-READABLE STORAGE MEDIUM

(71) Applicant: Olympus Corporation, Tokyo (JP)

(72) Inventor: Shintaro Inoue, Cambridge, MA (US)

(73) Assignee: OLYMPUS CORPORATION, Tokyo (JP)

(*) Notice: Subject to any disclaimer, the term of this patent is extended or adjusted under 35 U.S.C. 154(b) by 370 days.

(21) Appl. No.: 15/974,989

(22) Filed: May 9, 2018

(65) Prior Publication Data

US 2018/0256017 A1    Sep. 13, 2018

Related U.S. Application Data

(63) Continuation of application No. PCT/JP2015/082021, filed on Nov. 13, 2015.

(51) Int. Cl.
*A61B 1/00* (2006.01)
*A61B 1/05* (2006.01)
(Continued)

(52) U.S. Cl.
CPC ............ *A61B 1/053* (2013.01); *A61B 1/00* (2013.01); *A61B 1/00006* (2013.01);
(Continued)

(58) Field of Classification Search
None
See application file for complete search history.

(56) References Cited

U.S. PATENT DOCUMENTS 5,728,044 A * 3/1998 Shan .................... A61B 1/31
33/512
2005/0272971 A1    12/2005 Ohnishi et al.
(Continued)

FOREIGN PATENT DOCUMENTS

JP    2004-105725    4/2004
JP    2005-338551    12/2005
(Continued)

OTHER PUBLICATIONS

International Search Report dated Feb. 9, 2016 issued in PCT/JP2015/082021.
(Continued)

*Primary Examiner* — Timothy J Neal
(74) *Attorney, Agent, or Firm* — Scully, Scott, Murphy & Presser, P.C.

(57) ABSTRACT

The technology disclosed herein is directed to an endoscope system. The endoscope system includes an endoscope, a sensor; and a controller. The controller is configured to control the endoscope. The controller includes one or more processors. The one or more processors is configured (i) to extract first feature points from a first image captured by the endoscope, (ii) to extract second feature points from a second image captured by the endoscope after acquisition of the first image, (iii) to estimate a first result of position and orientation of the endoscope based on the first feature points and the second feature points, (iv) to calculate a first estimation accuracy based on the first result. When the first estimation accuracy is greater than a predetermined value, the one or more processors utilizes the first result as position and orientation of the endoscope.

13 Claims, 9 Drawing Sheets

(51) Int. Cl.
*G06T 7/73* (2017.01)
*G06T 7/70* (2017.01)
*A61B 1/045* (2006.01)

(52) U.S. Cl.
CPC .......... *A61B 1/00009* (2013.01); *A61B 1/045* (2013.01); *G06T 7/70* (2017.01); *G06T 7/73* (2017.01); *A61B 1/05* (2013.01); *G06T 2207/10016* (2013.01); *G06T 2207/10068* (2013.01); *G06T 2207/30244* (2013.01)

(56) References Cited

U.S. PATENT DOCUMENTS

| | | | |
|---|---|---|---|
| 2007/0265502 A1* | 11/2007 | Minosawa | A61B 17/3421 600/173 |
| 2011/0032347 A1* | 2/2011 | Lacey | A61B 5/065 348/68 |
| 2012/0062714 A1* | 3/2012 | Liu | G06T 7/75 348/65 |
| 2012/0121161 A1 | 5/2012 | Eade et al. | |
| 2013/0225981 A1 | 8/2013 | Hasegawa | |
| 2014/0180063 A1* | 6/2014 | Zhao | A61B 1/0005 600/424 |
| 2016/0154408 A1 | 6/2016 | Eade et al. | |
| 2016/0302653 A1 | 10/2016 | Inoue | |
| 2016/0353970 A1 | 12/2016 | Inoue | |

FOREIGN PATENT DOCUMENTS

| | | |
|---|---|---|
| JP | 2007-301378 | 11/2007 |
| JP | 2014-178328 | 9/2014 |
| JP | 2014-222551 | 11/2014 |
| JP | 2015-123201 | 7/2015 |
| WO | 2012-040644 | 3/2012 |
| WO | 2012117816 | 9/2012 |
| WO | 2012-125592 | 8/2015 |
| WO | 2015125592 | 8/2015 |

OTHER PUBLICATIONS

International Search Report and Written Opinion from corresponding International Application No. PCT/JP2015/082021, dated Feb. 9, 2016.

* cited by examiner

ENDOSCOPE SYSTEM, CONTROLLER, AND COMPUTER-READABLE STORAGE MEDIUM

CROSS-REFERENCE TO RELATED APPLICATION(S)

This application is a continuation application of PCT Application No. PCT/JP2015/082021 filed on Nov. 13, 2015, which is hereby incorporated by reference in its entirety.

TECHNICAL FIELD

The technology disclosed herein relates generally to a treatment system, and more particularly, some embodiments relate to a state estimation method of an endoscope.

DESCRIPTION OF THE RELATED ART

Generally, various methods are known for estimating the position, and orientation of an endoscope. For example, the following Japanese Patent Applications JP 2005-338551A, JP 2014-178328A, JP 2007-301378A, JP 2014-222551A, and WO patent Application 2012/117816A1 are cited for disclosing the general aspect of estimating the position and orientation of an endoscope.

BRIEF SUMMARY OF EMBODIMENTS

A first aspect of the technology disclosed herein is an endoscope system. The endoscope system comprises an endoscope, a sensor, and a controller. The controller is configured to control the endoscope. The controller comprises one or more processors. The one or more processors is configured (i) to extract first feature points from a first image captured by the endoscope; (ii) to extract second feature points from a second image captured by the endoscope after acquisition of the first image; (iii) to estimate a first result of position and orientation of the endoscope based on the first feature points and the second feature points; (iv) to calculate a first estimation accuracy based on the first result. When the first estimation accuracy is greater than a predetermined value, the one or more processors utilizes the first result as position and orientation of the endoscope.

A second aspect of the technology disclosed herein is a controller. The controller controls an endoscope including a sensor. The controller comprises one or more processors. The one or more processors is configured (i) to extract first feature points from a first image captured by the endoscope; (ii) to extract second feature points from a second image captured by the endoscope after acquisition of the first image; (iii) to estimate a first result of position and orientation of the endoscope based on the first feature points and the second feature points; (iv) to calculate a first estimation accuracy based on the first result. When the first estimation accuracy is greater than a predetermined value, the one or more processors utilizes the first result as position and orientation of the endoscope.

A third aspect of the technology disclosed herein is a non-transitory computer-readable medium storing a computer-readable program for implementing controlling method with an endoscope including a sensor. The method comprises (i) extracting first feature points from a first image captured by the endoscope; (ii) extracting second feature points from a second image captured by the endoscope after acquisition of the first image; (iii) estimating a first result of position and orientation of the endoscope based on the first feature points and the second feature points; (iv) calculating a first estimation accuracy based on the first result of position and orientation of the endoscope. When the first estimation accuracy is greater than a predetermined value, the method comprises adopting the first result as position and orientation of the endoscope.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

A first embodiment of the technology disclosed herein is directed to a state estimation method of an endoscope 2. The state estimation method is a method for estimating the state of the endoscope 2 in a treatment system 1. The state of the endoscope 2, for example, can be position, orientation, movement speed, acceleration, and the likes of the endoscope 2 during the operation of the endoscope 2 on a subject.

Figure 1:
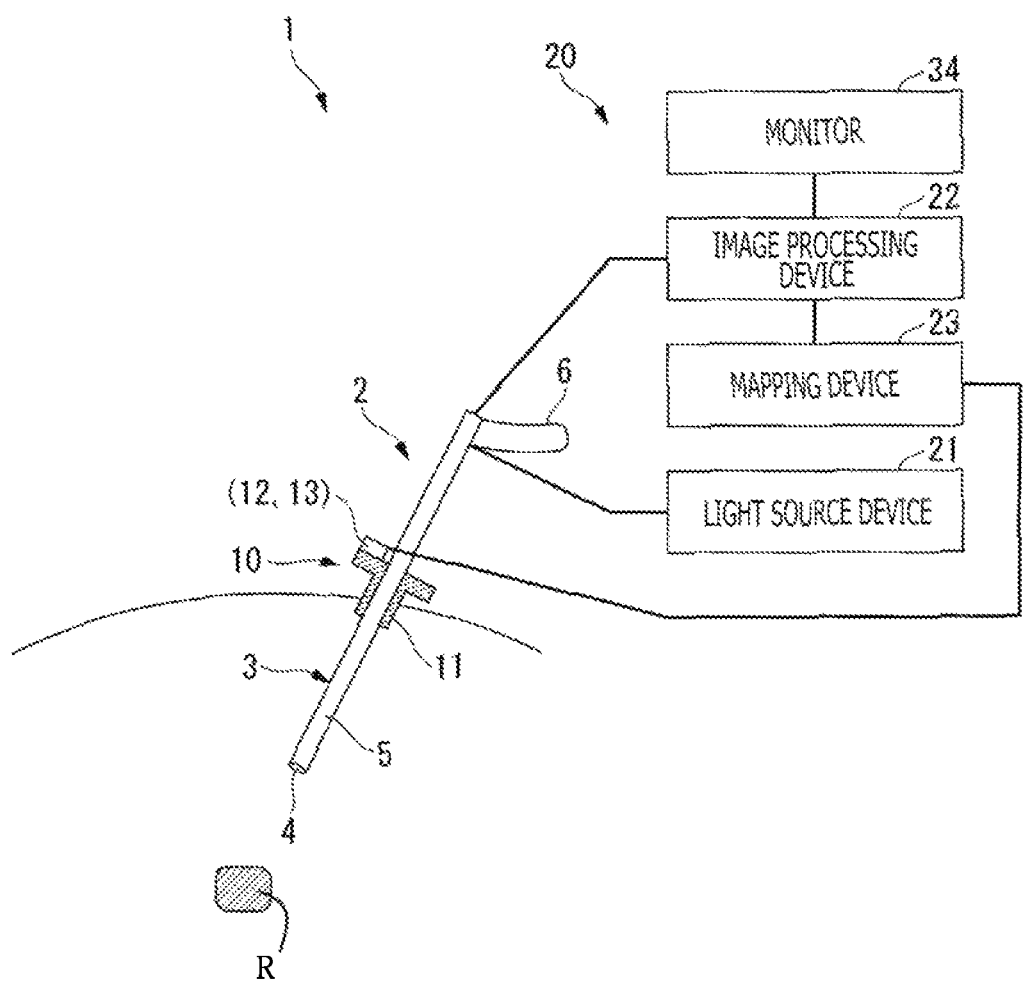
FIG. 1 is a schematic diagram of a treatment system to which a state estimation method of an endoscope in a first embodiment of the technology disclosed herein is applied.
Figure 2:
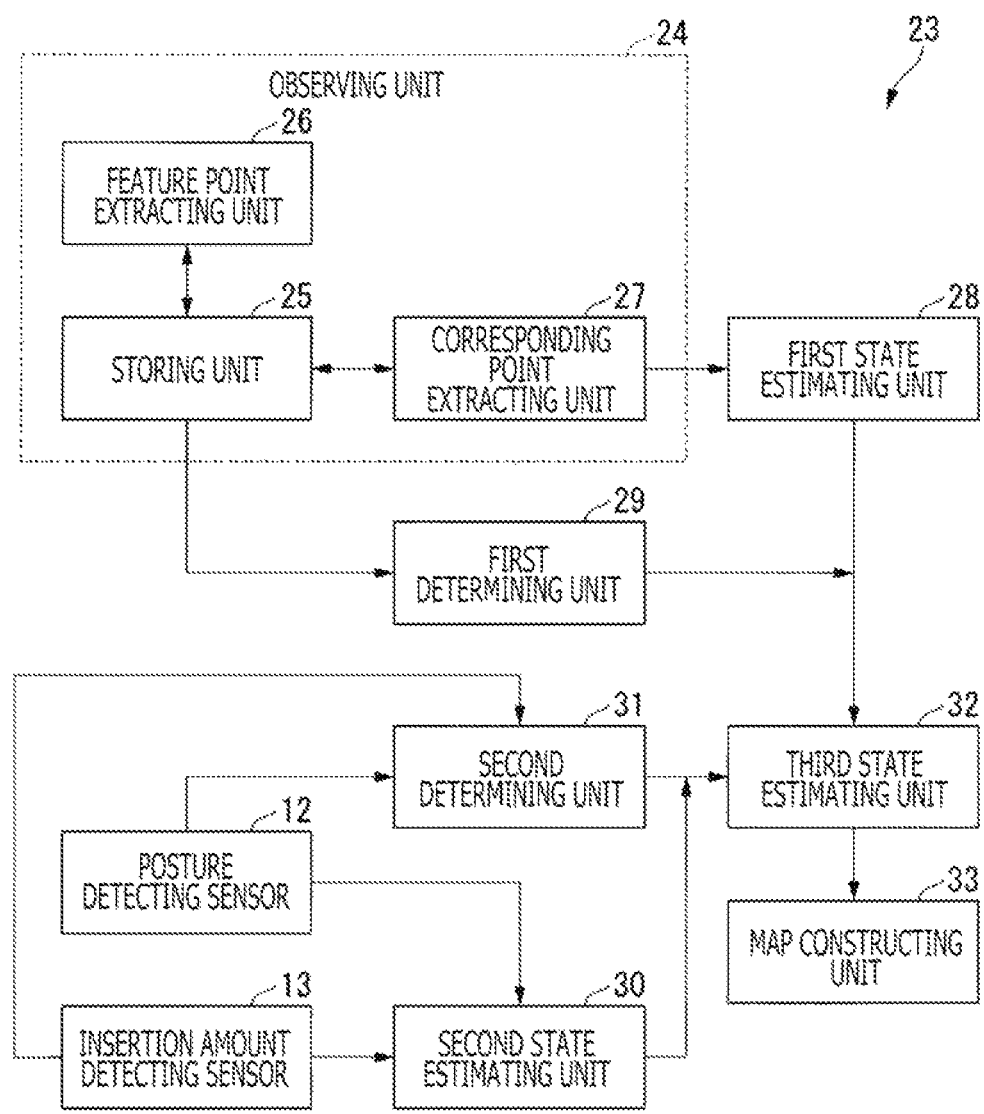
FIG. 2 is a block diagram of the treatment system in the first embodiment depicted in FIG. 1.
Figure 3:
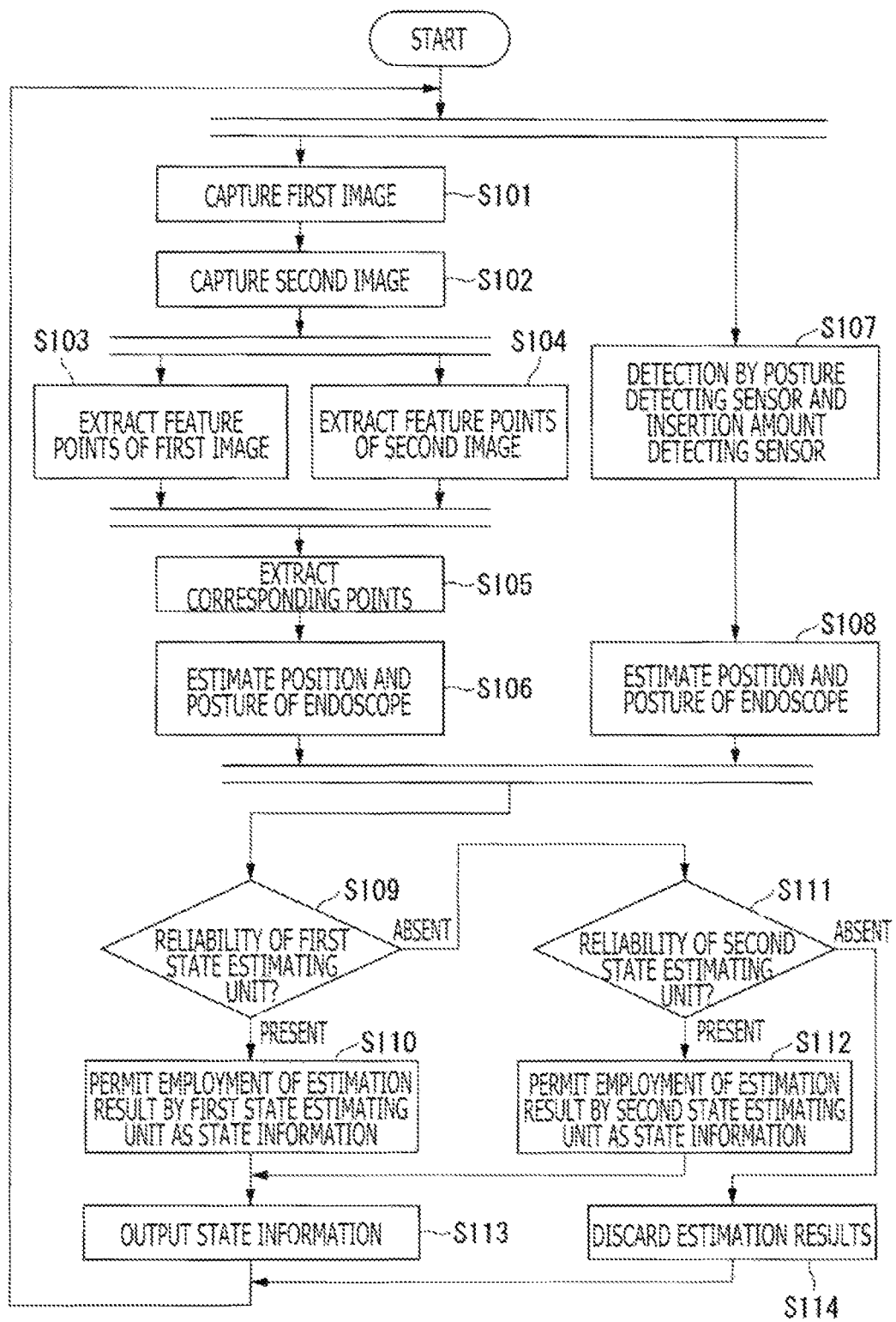
FIG. 3 is a flowchart depicting the state estimation method of an endoscope in the treatment system of the first embodiment.

One example of the treatment system 1 in the present embodiment is depicted in FIGS. 1-3 and is described hereinafter.

As depicted in FIG. 1, the treatment system 1 includes the endoscope 2, a sensing trocar 10, and a system main unit 20 (also referenced throughout this disclosure as controller). The endoscope 2 includes an insertion part 3 inserted into the body and a gripping part 6 disposed at an end part of the insertion part 3 to control and maneuver the insertion part 3. The insertion part 3 has a tubular shaft part 5 and an imaging unit 4 for observing the inside of the body of a patient or the like. The imaging unit 4 is electrically connected to or wirelessly communication with the system main unit 20. The imaging unit 4 acquires moving images and still images by capturing plural images at a predetermined frame rate in a first imaging step S101 and a second imaging step S102. For example, the imaging unit 4 acquires the moving images and still images of a region (R) inside of the body of the patient. The sensing trocar 10 is a tubular member for introducing the insertion part 3 of the endoscope 2 into the body. Moreover, the sensing trocar 10 has sensors for detecting the position and orientation of the endoscope 2. As one example, the sensing trocar 10 has a tubular part 11, an orientation detecting sensor 12, and an insertion amount detecting sensor 13. The tubular part 11 is attached to the abdominal wall of a patient. The orientation detecting sensor 12 detects the orientation of the sensing trocar 10. The insertion amount detecting sensor 13 detects the amount of insertion of the insertion part 3 with respect to the tubular part 11. The orientation detecting sensor 12 and the insertion amount detecting sensor 13 are electrically connected to the system main unit 20 and together they detect the position and orientation of the endoscope 2 in a detection step S107. The system main unit 20 includes a light source device 21, an image processing device 22, a mapping device 23, and a monitor 34. The light source device 21 is connected to the endoscope 2 in order to transmit illumination light thereto.

The image processing device 22 outputs an image captured by the endoscope 2 to the monitor 34 as a video signal. Furthermore, the image processing device 22 outputs the image captured by the endoscope 2 to the mapping device 23 as still image data. The mapping device 23 is electrically connected to the orientation detecting sensor 12 and the insertion amount detecting sensor 13 of the sensing trocar 10. Furthermore, the mapping device 23 is electrically connected to the image processing device 22. The mapping device 23 includes an observing unit 24, a first state estimating unit 28, a first determining unit 29, a second state estimating unit 30, a second determining unit 31, a third state estimating unit 32, and a map constructing unit 33. The observing unit 24 is connected to the image processing device 22. Furthermore, the observing unit 24 is connected to the first state estimating unit 28 and the first determining unit 29. The observing unit 24 includes a storing unit 25, a feature point extracting unit 26, and a corresponding point extracting unit 27. The storing unit 25 stores pieces of still image data output from the image processing device 22 and data calculated by the observing unit 24.

The feature point extracting unit 26 uses two pieces of still image data to extract feature points in the respective pieces of still image data. The two pieces of still image data are a first image and a second image. The two pieces are separate by a predetermined time or a predetermined number of frames among the pieces of still image data output from the image processing device 22. The feature point extracting unit 26 extracts feature points in the first image and feature points in the second image and causes the storing unit 25 to store the feature points. The feature point extracting unit 26 includes two feature point extraction engines that concurrently operate. In the present embodiment, one feature point extraction engine is assigned to extraction processing of feature points from one piece of still image data in a first extraction step S103 and a second extraction step S104. Due to this configuration, delay in the processing execution occurs less readily even when the number of feature points in the still image data is enormous. The corresponding point extracting unit 27 reads the respective feature points in the respective first and second images and associates the feature points in the first image with the feature points in the second image. The corresponding point extracting unit 27 carries out extraction of corresponding points by a feature point extraction algorithm such as the scale-invariant feature transform, or SIFT, or speeded up robust features, or SURF, for example. The corresponding point extracting unit 27 carries out the extraction of corresponding points and causes the storing unit 25 to store the coordinates of the corresponding points and the number of corresponding points in a third extraction step S105.

The first state estimating unit 28 reads the coordinates of the corresponding points from the storing unit 25 and calculates the amount of movement of the endoscope 2 from the time of the acquisition of the first image to the time of the acquisition of the second image. Moreover, the first state estimating unit 28 estimates, in a first estimation step S106, the position and orientation of the endoscope 2 at the time of the acquisition of the second image based on (1) the position and orientation of the endoscope 2 at the time of the acquisition of the first image and (2) the amount of movement of the endoscope calculated as described hereinbefore. The first state estimating unit 28 outputs the estimation result to the third state estimating unit 32.

The first determining unit 29 reads the number of corresponding points from the storing unit 25 and determines whether or not the number of corresponding points is equal to or larger than a predetermined threshold in a first determination step S109. The predetermined threshold in the first determining unit 29 is set in advance based on the smallest number of corresponding points with which calculation of the amount of movement of the endoscope 2 is allowed. If the number of corresponding points is equal to or larger than the predetermined threshold, the first determining unit 29 determines that reliability is present in the estimation result by the first state estimating unit 28, and permits the third state estimating unit 32 to utilize the estimation result by the first state estimating unit 28 in a step S110. If the number of corresponding points is smaller than the predetermined threshold, the first determining unit 29 determines that reliability is absent in the estimation result by the first state estimating unit 28, and prohibits the third state estimating unit 32 from utilizing the estimation result by the first state estimating unit 28. The case in which the number of corresponding points is smaller than the predetermined threshold is the case in which a part common to the first image and the second image is absent and corresponding points do not exist. For example, the case in which the first image or the second image is captured in the state in which the field of view is poor due to smoke or mist, or the like. The second state estimating unit 30 is electrically connected to the orientation detecting sensor 12 and the insertion amount detecting sensor 13 of the sensing trocar 10. The second state estimating unit 30 is configured to receive a first value that is detected by the orientation detecting sensor 12. The second state estimating unit 30 is configured to receive a second value that is detected by the insertion amount detecting sensor 13. Based on the result of the detection in the detection step S107 by the orientation detecting sensor 12 and the insertion amount detecting sensor 13, the second state estimating unit 30 estimates the position and orientation of the endoscope 2 in a second estimation step S108. The second state estimating unit 30 outputs the estimation result to the third state estimating unit 32.

The second determining unit 31 is electrically connected to the orientation detecting sensor 12 and the insertion amount detecting sensor 13 of the sensing trocar 10. The second determining unit 31 determines, in a second determination step S111, whether reliability of the estimation in the second state estimating unit 30 is present or absent by determining whether or not the detection result acquired from the orientation detecting sensor 12 and the insertion amount detecting sensor 13 has received the influence of disturbance or the like. For example, if both the orientation detecting sensor 12 and the insertion amount detecting sensor 13 indicate a detection result in the normal range, the second determining unit 31 determines that (1) both the orientation detecting sensor 12 and the insertion amount detecting sensor 13 have not received the influence of disturbance or the like and (2) reliability is present in the estimation result by the second state estimating unit 30. Then the second determining unit 31 permits the third state estimating unit 32 to utilize the estimation result by the second state estimating unit 30 in a step S112. If at least either the orientation detecting sensor 12 or the insertion amount detecting sensor 13 indicates an abnormal value due to the influence of disturbance or the like, the second determining unit 31 determines that reliability is absent in the estimation result by the second state estimating unit 30, and prohibits the third state estimating unit 32 from utilizing the estimation result by the second state estimating unit 30.

The third state estimating unit 32 accepts the estimation result output from the first state estimating unit 28 and the estimation result output from the second state estimating unit 30. The third state estimating unit 32 utilizes the estimation result permitted to be utilized as state information of the endoscope 2 based on the determination result in the first determining unit 29 and the second determining unit 31. Then the third state estimating unit 32 outputs the state information of the endoscope 2 to the map constructing unit 33 in a third estimation step S113, or a calculation step thereof. The state information in the present embodiment includes information on the position and orientation of the endoscope 2. However, one of ordinary skill in the art would appreciate that that process steps can be applied to other condition or movement of the endoscope during the operation on the patient. If both the estimation result by the first state estimating unit 28 and the estimation result by the second state estimating unit 30 have reliability, the third state estimating unit 32 utilizes either one of the estimation result by the first state estimating unit 28 and the estimation result by the second state estimating unit 30 in accordance with the order of priority defined in advance. For example, in the present embodiment, the third state estimating unit 32 utilizes the estimation result by the first state estimating unit 28 if both the estimation result by the first state estimating unit 28 and the estimation result by the second state estimating unit 30 have reliability. Furthermore, if neither the estimation result by the first state estimating unit 28 nor the estimation result by the second state estimating unit 30 has reliability, both the estimation result by the first state estimating unit 28 and the estimation result by the second state estimating unit 30 are discarded in a step S114.

The map constructing unit 33 constructs a map of the target imaged by using the endoscope 2 and estimates the position and orientation of the endoscope 2 in the constructed map. As one example, the mapping device 23 carries out the construction of a map of the inside of the body of the patient and the estimation of the position and orientation of the endoscope 2 by a Visual Simultaneous Localization and Mapping, or VSLAM, technique with use of the image captured by the imaging unit 4. In the present embodiment, if the third state estimating unit 32 utilizes the estimation result by the first state estimating unit 28, the mapping device 23 carries out the construction of the map of the inside of the body of the patient and the estimation of the position and orientation of the endoscope 2 by using the image captured by the imaging unit 4, or the first image or the second image. Furthermore, in the present embodiment, if the third state estimating unit 32 utilizes the estimation result by the second state estimating unit 30, the mapping device 23 has a pause in constructing the map of the inside of the body and carries out estimation of the position and orientation of the endoscope 2 in an already-constructed map. The map of the inside of the body of the patient constructed by the map constructing unit 33 may be allowed to be turned to an image and be output to the monitor 34 via the image processing device 22.

In the present embodiment, the position and orientation of the endoscope 2 can be estimated by using the image captured by the imaging unit 4. In addition, the position and orientation of the endoscope 2 can be estimated by using the orientation detecting sensor 12 and the insertion amount detecting sensor 13 disposed in the sensing trocar 10. Furthermore, in the present embodiment, the estimation result of the position and orientation of the endoscope 2 by use of the orientation detecting sensor 12 and the insertion amount detecting sensor 13 is automatically utilized by the third state estimating unit 32 if reliability of the estimation of the position and orientation of the endoscope 2 by use of the image captured by the imaging unit 4 is absent. Thus, the estimation of the position and orientation of the endoscope 2 is suspended less readily. Moreover, in the present embodiment, the estimation result of the position and orientation of the endoscope 2 by use of the image captured by the imaging unit 4 is automatically utilized by the third state estimating unit 32 if reliability of the estimation of the position and orientation of the endoscope 2 by use of the orientation detecting sensor 12 and the insertion amount detecting sensor 13 is absent. Thus, the estimation of the position and orientation of the endoscope 2 is suspended less readily.

As noted hereinbefore, in the present embodiment, the state estimating units of two systems, or the first state estimating unit 28 and the second state estimating unit 30, complement each other regarding the estimation of the position and orientation of the endoscope 2. Therefore, robustness against disturbance is high. The first state estimating unit 28 and the second state estimating unit 30 may be configured to cause the estimation result to include the movement speed of the endoscope 2, the angular velocity of the endoscope 2, the acceleration of the endoscope 2, and so forth besides the position and orientation of the endoscope 2. In addition, the sensing trocar 10 may include sensors such as acceleration sensor, gyro sensor, and geomagnetic sensor and the likes.

Furthermore, as determination criteria for determining whether reliability is present or absent in the first determining unit 29, (1) the amount of movement of the corresponding point, (2) the correlativity of movement vectors of the corresponding points in the first image and the second image, (3) the degree of blur in the first image and the second image, (4) the degree of poorness of the field of view due to smoke or the like in the first image and the second image, (5) the degree of poorness of the field of view due to halation or the like in the first image and the second image, and so forth may be included besides the number of corresponding points. The amount of movement of the corresponding point can be difference between the coordinates of the corresponding point in the first image and the coordinates of the corresponding point in the second image. Moreover, the sensing trocar 10 may include three or more sensors different from each other in the principle of detection. As a determination method for determining whether reliability is present or absent in the second determining unit 31, even when one of the three sensors indicates an abnormal value, the second determining unit 31 may determine that the estimation result has reliability if the other two sensors fall within the normal range. In addition, the insertion part 3 of the endoscope 2 may have an active curving part. In this case, it is preferable that the endoscope 2 include a sensor for detecting the curving state of the active curving part of the endoscope 2 and this sensor be electrically connected to the mapping device 23 similarly to the respective sensors of the sensing trocar 10.

Figure 4:
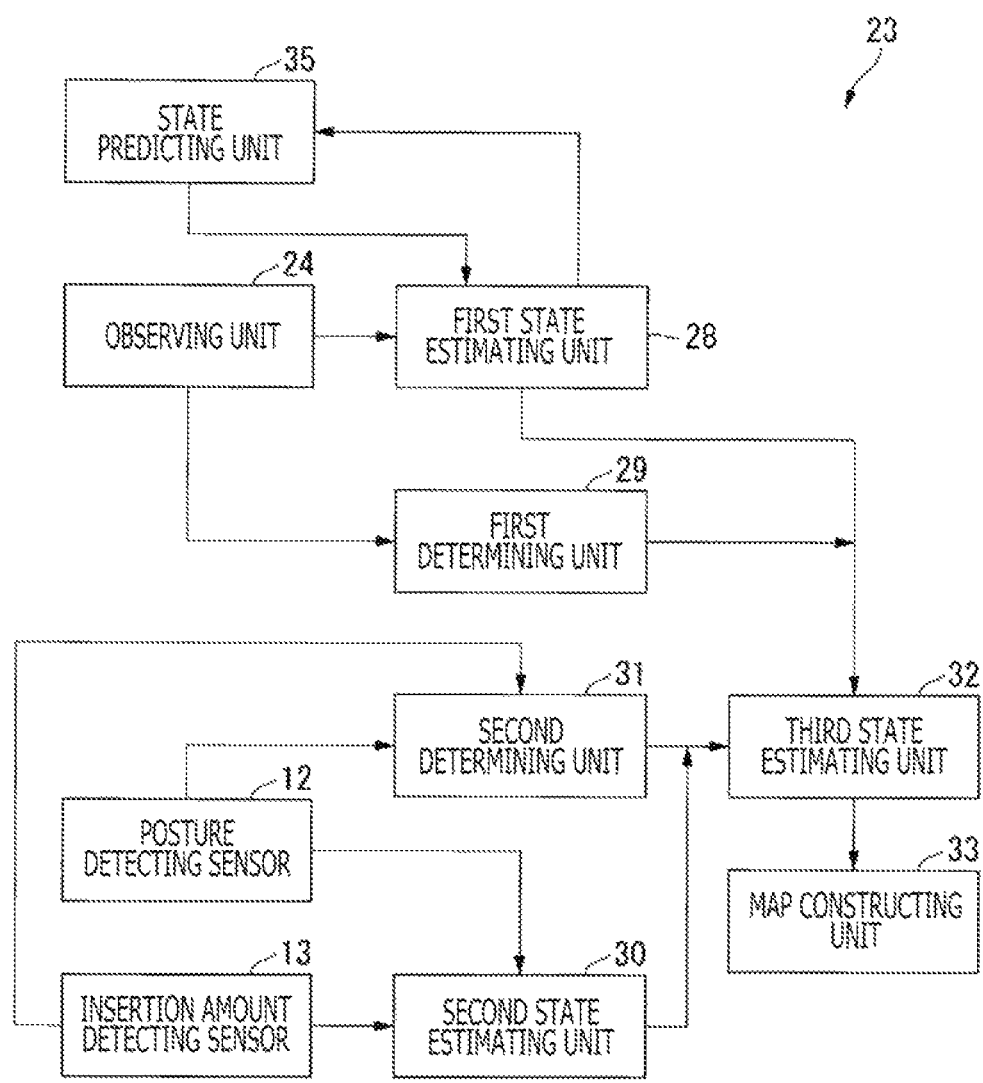
FIG. 4 is a block diagram depicting the configuration of a modification example of the first embodiment.

A modification example of the above-described embodiment is described by using FIG. 4. The present modification example is different from the above-described first embodiment in that the mapping device 23 includes a state predicting unit 35. The state predicting unit 35 is connected to the first state estimating unit 28 and accepts the estimation result by the first state estimating unit 28 to predict the position and orientation of the endoscope 2. In this case, by predicting the position and orientation of the endoscope 2 in advance, the amount of calculation of the state information can be reduced compared with the case in which only information on the coordinates of corresponding points extracted by the observing unit 24 is used.

Figure 5:
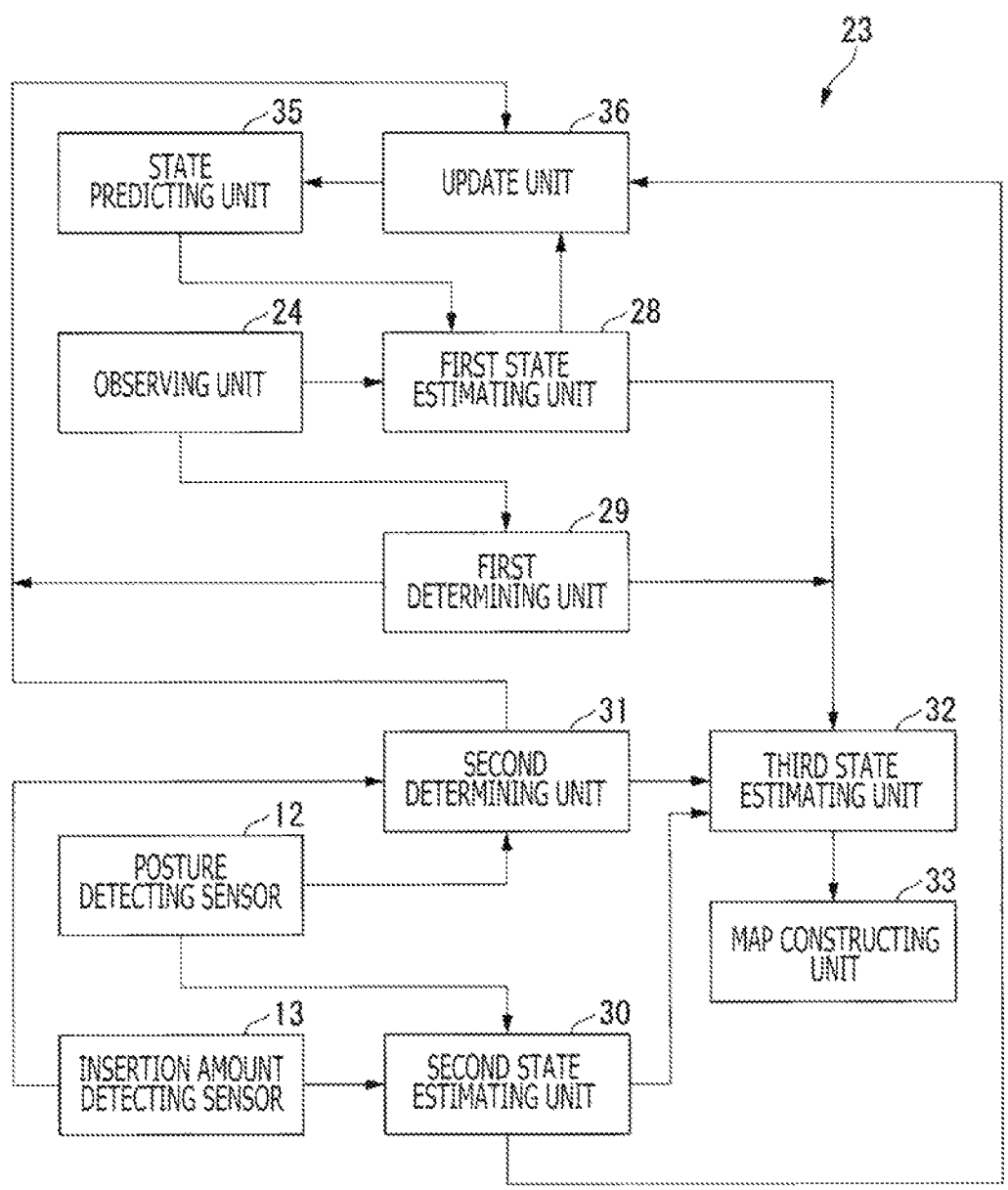
FIG. 5 is a block diagram of a treatment system to which a state estimation method of an endoscope in a second embodiment of the technology disclosed herein is applied.
Figure 6:
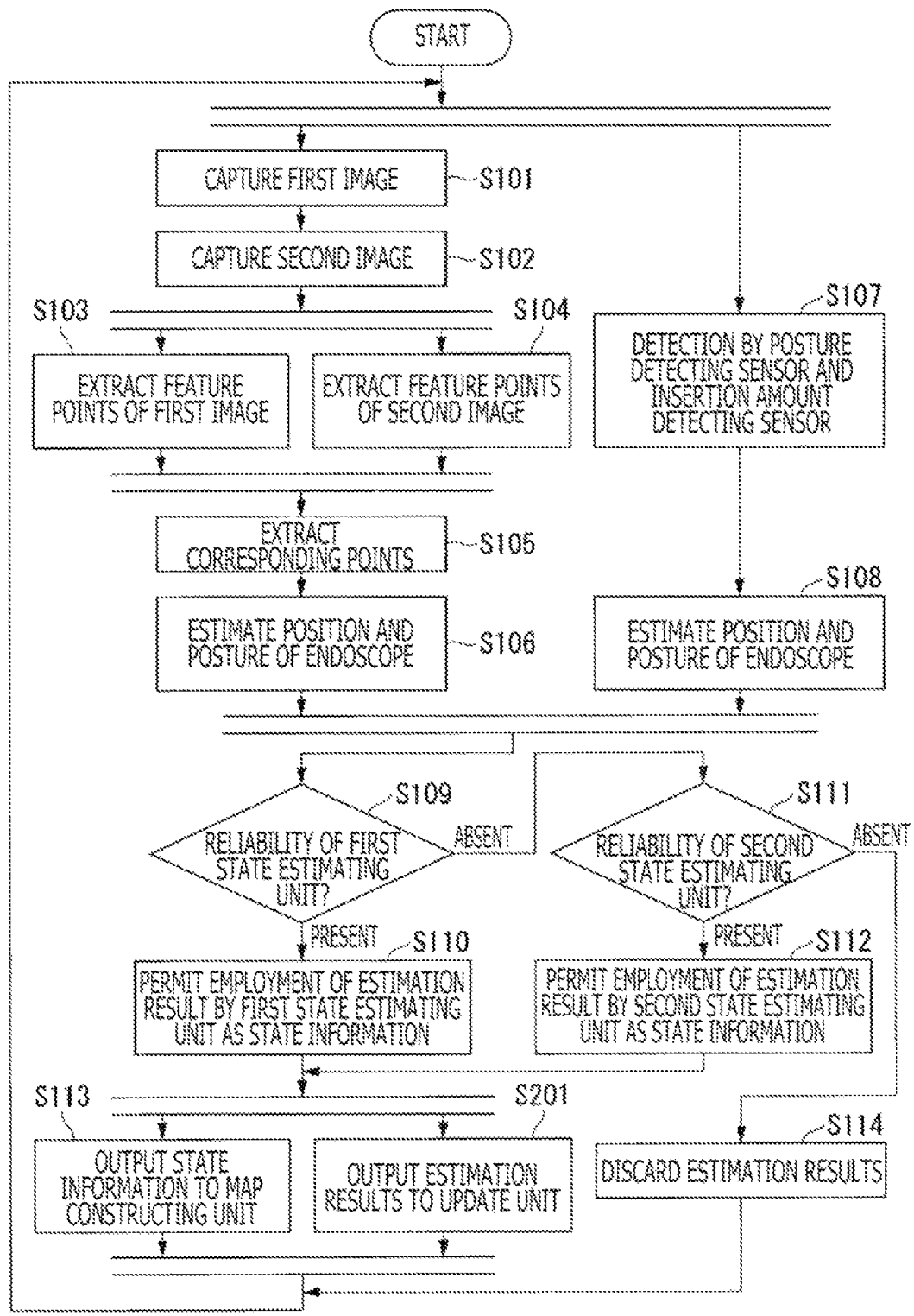
FIG. 6 is a flowchart depicting the state estimation method of an endoscope in the treatment system of the second embodiment.

A second embodiment of the technology disclosed herein is described by referring to FIGS. 5 and 6. In the following respective embodiments, a constituent element that is similar to or corresponds to the first embodiment is given the same numeral as the first embodiment and overlapping description is omitted to avoid redundancy. Furthermore, also regarding steps of state estimation methods of an endoscope in the following respective embodiments, processing similar to processing in the first embodiment is given the same numeral as the first embodiment similarly. In the present embodiment, compared with the above-described modification example of the first embodiment, an update unit 36 intervenes between the first state estimating unit 28 and the state predicting unit 35. The second state estimating unit 30 is connected to the update unit 36. The first state estimating unit 28 and the second state estimating unit 30 output estimation results to the update unit 36 in a step S201. Furthermore, the first determining unit 29 and the second determining unit 31 are connected to the third state estimating unit 32 similarly to the above-described first embodiment and are further connected also to the above-described update unit 36. The update unit 36 selects the estimation result having reliability in the estimation result by the first state estimating unit 28 and the estimation result by the second state estimating unit 30. The update unit 36 outputs the selected estimation result to the state predicting unit 35. Determination of whether reliability is present or absent in the update unit 36 obeys the determination result in the first determining unit 29 and the second determining unit 31. In the present embodiment, for example, if the estimation result by the first state estimating unit 28 does not have reliability, the estimation result by the second state estimating unit 30 is input to the state predicting unit 35. Thus, in the present embodiment, it is possible to prevent the state predicting unit 35 from carrying out prediction based on the estimation result having low reliability.

Figure 7:
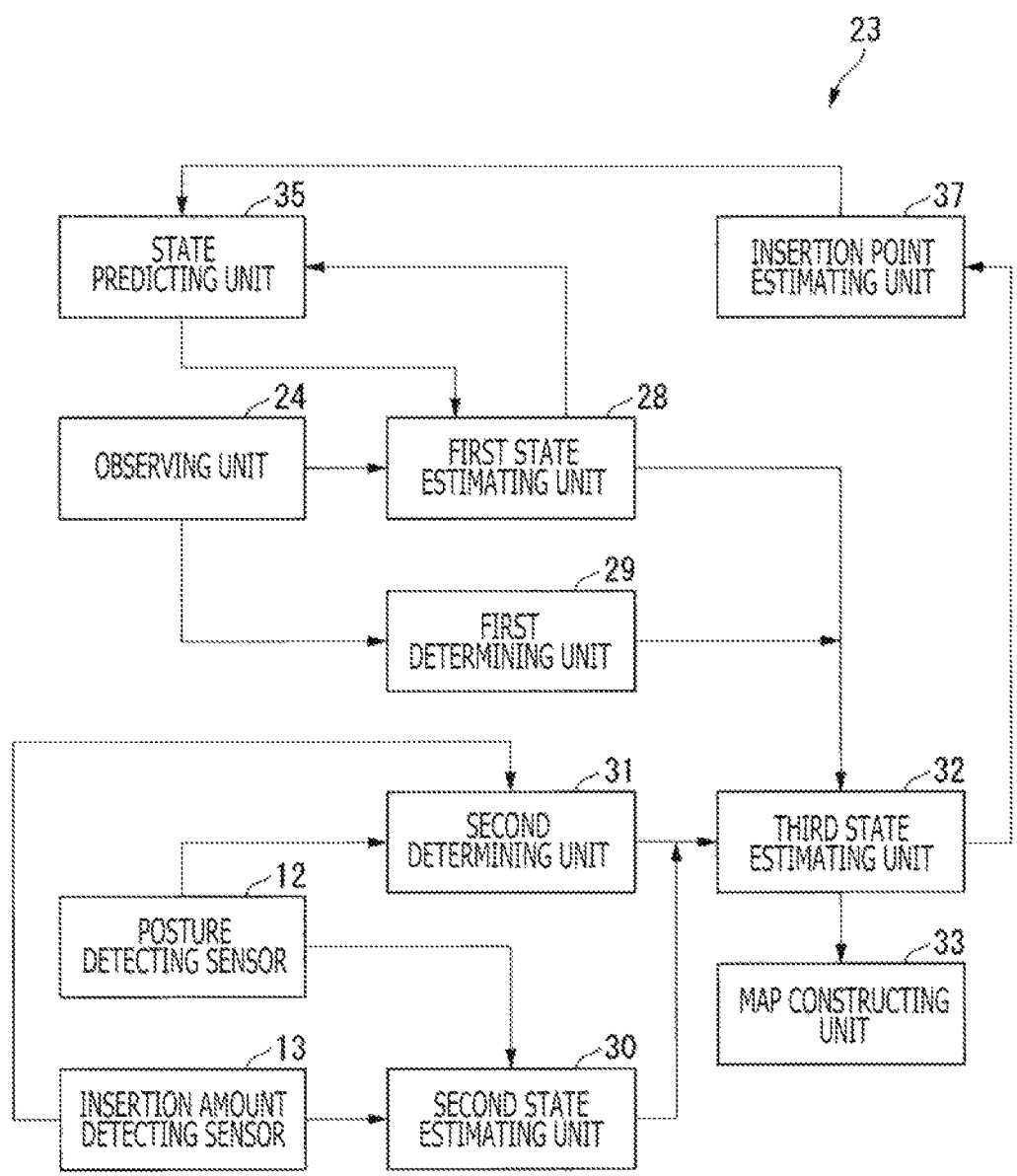
FIG. 7 is a block diagram of a treatment system to which a state estimation method of an endoscope in a third embodiment of the technology disclosed herein is applied.
Figure 8:
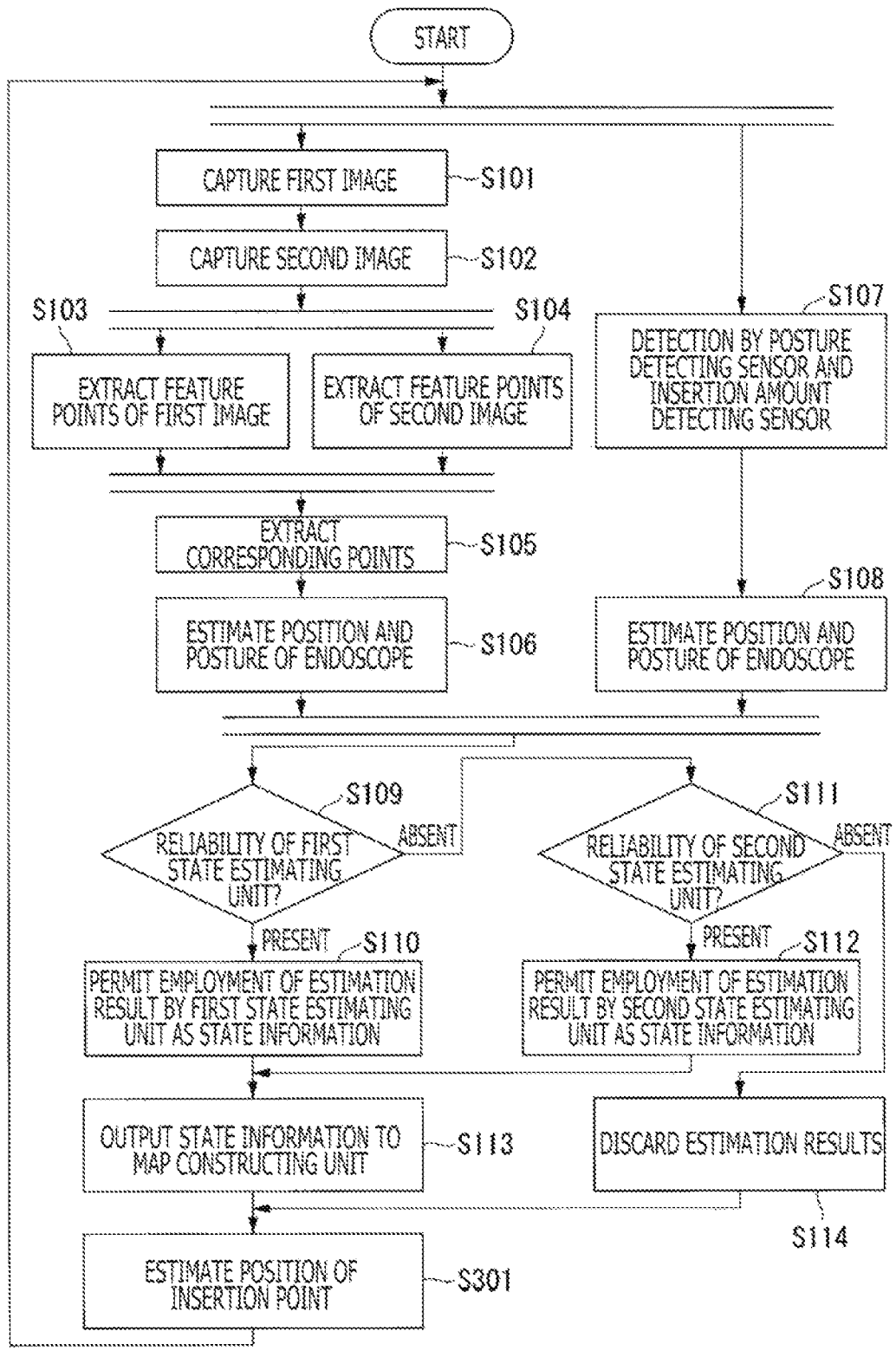
FIG. 8 is a flowchart depicting the state estimation method of an endoscope in this treatment system of the third embodiment.

A third embodiment of the technology disclosed herein is described by referring to FIGS. 7 and 8. Compared with the above-described modification example of the first embodiment, the present embodiment is different in that the mapping device 23 further includes an insertion point estimating unit 37 connected to the third state estimating unit 32 and the state predicting unit 35. The insertion point estimating unit 37 estimates the position at which the sensing trocar 10 is indwelled on a body wall of the patient by using state information output from the third state estimating unit 32 in an insertion point position estimation step S301. The position at which the sensing trocar 10 is indwelled on a body wall in the present embodiment is the position of the insertion point of the endoscope 2 into the body. If the position of the insertion point is estimated in the insertion point estimating unit 37, the state predicting unit 35 deems that the endoscope 2 swings with the insertion point being the center of the swing, and limits the calculation range of the prediction. In the present embodiment, the movement of the endoscope 2 is limited by the sensing trocar 10 and therefore there is no need to predict movement of the endoscope 2 with which the position of the sensing trocar 10, or the insertion point, greatly moves. For this reason, the amount of calculation of the state information can be reduced to a large extent by estimating the position of the insertion point by the insertion point estimating unit 37. Moreover, the accuracy of the predictive model can be enhanced because prediction based on the assumption that the endoscope 2 swings with the insertion point being the center of the swing can be carried out. As a result, according to the present embodiment, the position and orientation of the endoscope 2 can be estimated with high accuracy in a short time.

Figure 9:
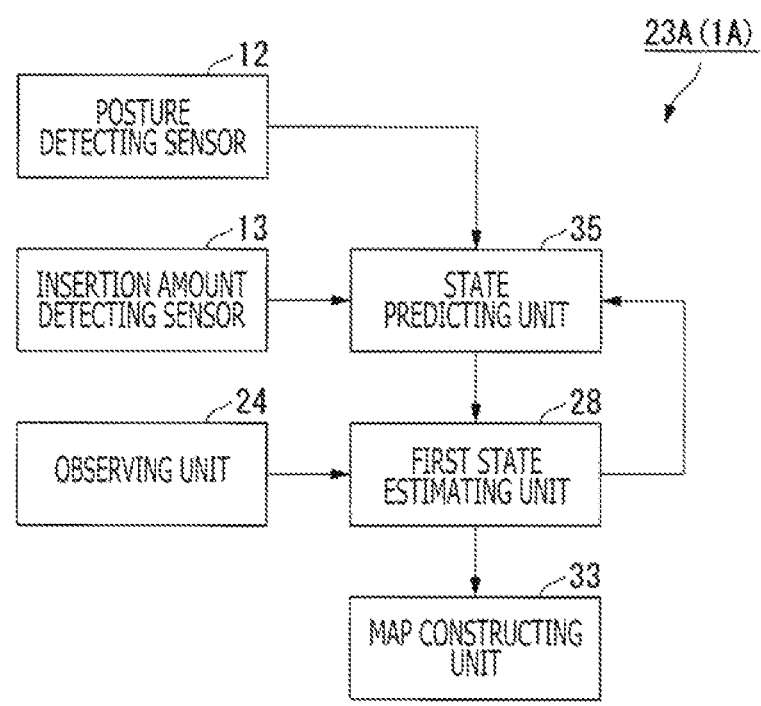
FIG. 9 is a block diagram of a treatment system to which a state estimation method of an endoscope in a fourth embodiment of the technology disclosed herein is applied.

A fourth embodiment of the technology disclosed herein is described by referring to FIG. 9. A treatment system 1A of the present embodiment includes a mapping device 23A whose configuration is different from the mapping device 23 disclosed in the above-described respective embodiments. Furthermore, the mapping device 23A estimates the state of the endoscope 2 by a different method from the mapping device 23 disclosed in the above-described respective embodiments. In the present embodiment, the orientation detecting sensor 12 and the insertion amount detecting sensor 13 disposed in the sensing trocar 10 are connected to the state predicting unit 35. Furthermore, the mapping device 23A of the present embodiment does not have the first determining unit 29, the second determining unit 31, the second state estimating unit 30, and the third state estimating unit 32 as depicted, for example, in FIG. 2. Moreover, in the present embodiment, the estimation result by the first state estimating unit 28 is output to the map constructing unit 33 as state information of the endoscope 2. In the present embodiment, the detection result by the orientation detecting sensor 12 and the insertion amount detecting sensor 13 disposed in the sensing trocar 10 complements the estimation result by the first state estimating unit 28 in processing of prediction in the state predicting unit 35. Due to this configuration, the prediction accuracy can be made higher than in prediction in which only the estimation result by the first state estimating unit 28 is used. In the present embodiment, it is not essential that the sensing trocar 10 includes both the orientation detecting sensor 12 and the insertion amount detecting sensor 13. As long as (1) one or more sensors are attached to the sensing trocar 10 or the endoscope 2 and (2) information on the position, orientation, movement speed, angular velocity, acceleration, or the like of the endoscope 2 can be output to the state predicting unit 35, the state predicting unit 35 can carry out prediction with higher accuracy than in prediction in which only the estimation result by the first state estimating unit 28 is used.

In the embodiments described above, the system main unit 20 can be realized by hardware such as one or more Central Processing Unit (CPU), and by reading instructions stored on a computer readable storage device.

The embodiments of the present disclosure are described in detail hereinbefore with reference to the drawings. However, various configurations are not limited to these embodiments and design changes and so forth in such a range as not to depart from the gist of the technology disclosed herein are also included. As one of ordinary skill in the art would appreciate that the technology disclosed herein can be used for an endoscope and/or a system including an endoscope.

In sum, the technology disclosed herein is directed to an endoscope system having an endoscope and a controller configured to control the endoscope. The controller comprises one or more processors configured to extract first feature points from a first image captured by the endoscope, to extract second feature points from a second image captured by the endoscope after acquisition of the first image, to estimate a first result of position and orientation of the endoscope based on the first feature points and the second feature points, and to calculate a first estimation accuracy based on the first result of position and orientation of the endoscope. And when the first estimation accuracy is greater than a predetermined value, the one or more processors is configured to utilize the first result as position and orientation of the endoscope.

The endoscope system further includes a sensor configured to detect at least one of position, orientation, movement speed, and acceleration of the endoscope. The sensor is attached to at least one of the endoscope and a trocar. When the first estimation accuracy is equal to or smaller than the predetermined value, the one or more processors is further configured to receive a first value detected by the sensor at the time of capturing the first image, to receive a second value detected by the sensor at the time of capturing the second image, to estimate a second result of position and orientation of the endoscope based on the first value and the second value, and to calculate a second estimation accuracy based on the second result, so that when the second estimation accuracy is greater than the predetermined value, the one or more processors is configured to utilize the second result as position and orientation of the endoscope. The one or more processors is further configured to estimate a position of an insertion point of the endoscope into a body of the patient based on the first result or the second result. The one or more processors is configured to extract coordinates of corresponding points by associating the first feature points with the second feature points and to estimate the first result based on the coordinates of the corresponding points.

A controller for controlling an endoscope system having an endoscope. The controller comprises one or more processors being configured to extract first feature points from a first image captured by the endoscope, to extract second feature points from a second image captured by the endoscope after acquisition of the first image, to estimate a first result of position and orientation of the endoscope based on the first feature points and the second feature points and to calculate a first estimation accuracy based on the first result of position and orientation of the endoscope. When the first estimation accuracy is greater than a predetermined value, the one or more processors is configured to utilize the first result as position and orientation of the endoscope. The one or more processors is further configured so that when the first estimation accuracy is equal to or smaller than the predetermined value, to receive a first value detected by a sensor at the time of capturing the first image, to receive a second value detected by the sensor at the time of capturing the second image, to estimate a second result of position and orientation of the endoscope based on the first value and the second value. And to calculate a second estimation accuracy based on the second result so that when the second estimation accuracy is greater than the predetermined value, the one or more processors is configured to utilize the second result as position and orientation of the endoscope and the sensor is configured to detect at least one of position, orientation, movement speed, and acceleration of the endoscope. The one or more processors is further configured to estimate a position of an insertion point of the endoscope into a body of patient based on the first result or the second result. The one or more processors is configured to extract coordinates of corresponding points by associating the first feature points with the second feature points and to estimate the first result based on the coordinates of the corresponding points. The sensor is attached to at least one of the endoscope and a trocar.

A non-transitory computer-readable medium storing a computer-readable program for implementing controlling method with an endoscope system including an endoscope. The method comprises extracting first feature points from a first image captured by the endoscope, extracting second feature points from a second image captured by the endoscope after acquisition of the first image, estimating a first result of position and orientation of the endoscope based on the first feature points and the second feature points, and calculating a first estimation accuracy based on the first result of position and orientation of the endoscope so that when the first estimation accuracy is greater than a predetermined value, utilizing the first result as position and orientation of the endoscope. In the non-transitory computer-readable medium when the first estimation accuracy is equal to or smaller than the predetermined value, the method further comprises receiving a first value detected by a sensor at the time of capturing the first image, receiving a second value detected by the sensor at the time of capturing the second image, estimating a second result of position and orientation of the endoscope based on the first value and the second value, and calculating a second estimation accuracy based on the second result so that when the second estimation accuracy is greater than the predetermined value, utilizing the second result as position and orientation of the endoscope, and the sensor is configured to detect at least one of position, orientation, movement speed, and acceleration of the endoscope. In the non-transitory computer-readable medium, the method further comprises estimating a position of an insertion point of the endoscope into a body of patient based on the first result or the second result. The method comprises extracting coordinates of corresponding points by associating the first feature points with the second feature points, and estimating the first result based on the coordinates of the corresponding points.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope system comprising:
   an endoscope;
   a sensor configured to detect at least one of position, orientation, movement speed, and acceleration of the endoscope; and
   a controller configured to control the endoscope, the controller comprises one or more processors, wherein the one or more processors being configured to:
      extract first feature points from a first image captured by the endoscope,
      extract second feature points from a second image captured by the endoscope after acquisition of the first image,
      estimate a first result of position and orientation of the endoscope based on the first feature points and the second feature points, and
      calculate a first estimation accuracy based on the first result of position and orientation of the endoscope, and
   wherein when the first estimation accuracy is greater than a predetermined value, the one or more processors is configured to utilize the first result as position and orientation of the endoscope.

2. The endoscope system according to claim 1, wherein the sensor is attached to at least one of the endoscope and a trocar.

3. The endoscope system according to claim 1, wherein when the first estimation accuracy is equal to or smaller than the predetermined value, the one or more processors being further configured to:
   receive a first value detected by the sensor at the time of capturing the first image, and receive a second value detected by the sensor at the time of capturing the second image,
   estimate a second result of position and orientation of the endoscope based on the first value and the second value, and
   calculate a second estimation accuracy based on the second result, so that when the second estimation accuracy is greater than the predetermined value, the one or more processors is configured to utilize the second result as position and orientation of the endoscope.

4. The endoscope system according to claim 3, wherein the one or more processors being further configured to estimate a position of an insertion point of the endoscope into a body of the patient based on the first result or the second result.

5. The endoscope system according to claim 1, wherein the one or more processors being configured to:
   extract coordinates of corresponding points by associating the first feature points with the second feature points; and
   estimate the first result based on the coordinates of the corresponding points.

6. A controller for controlling an endoscope system including an endoscope, the controller comprising:
   one or more processors being configured to:
   extract first feature points from a first image captured by the endoscope;
      extract second feature points from a second image captured by the endoscope after acquisition of the first image;
      estimate a first result of position and orientation of the endoscope based on the first feature points and the second feature points; and
      calculate a first estimation accuracy based on the first result of position and orientation of the endoscope,
   wherein when the first estimation accuracy is greater than a predetermined value, the one or more processors is configured to utilize the first result as position and orientation of the endoscope, wherein, when the first estimation accuracy is equal to or smaller than the predetermined value, the one or more processors being further configured to:
receive a first value detected by a sensor at the time of capturing the first image;
receive a second value detected by the sensor at the time of capturing the second image;
estimate a second result of position and orientation of the endoscope based on the first value and the second value; and
calculate a second estimation accuracy based on the second result, so that when the second estimation accuracy is greater than the predetermined value: the one or more processors is configured to utilize the second result as position and orientation of the endoscope, and
wherein the sensor is configured to detect at least one of position, orientation, movement speed, and acceleration of the endoscope.

7. The controller according to claim 6, wherein the one or more processors being further configured to estimate a position of an insertion point of the endoscope into a body of patient based on the first result or the second result.

8. The controller according to claim 6, wherein the one or more processors being configured to:
extract coordinates of corresponding points by associating the first feature points with the second feature points; and
estimate the first result based on the coordinates of the corresponding points.

9. The controller according to claim 6, wherein the sensor is attached to at least one of the endoscope and a trocar.

10. A non-transitory computer-readable medium storing a computer-readable program for implementing controlling a method with an endoscope system including an endoscope, the method comprising:
extracting first feature points from a first image captured by the endoscope;
extracting second feature points from a second image captured by the endoscope after acquisition of the first image;
estimating a first result of position and orientation of the endoscope based on the first feature points and the second feature points; and
calculating a first estimation accuracy based on the first result of position and orientation of the endoscope so that when the first estimation accuracy is greater than a predetermined value, utilizing the first result as position and orientation of the endoscope,
wherein, when the first estimation accuracy is equal to or smaller than the predetermined value, the method further comprising:
receiving a first value detected by a sensor at the time of capturing the first image;
receiving a second value detected by the sensor at the time of capturing the second image; estimating a second result of position and orientation of the endoscope based on the first value and the second value; and
calculating a second estimation accuracy based on the second result, so that when the second estimation accuracy is greater than the predetermined value, utilizing the second result as position and orientation of the endoscope, and
wherein the sensor is configured to detect at least one of position, orientation, movement speed, and acceleration of the endoscope.

11. The non-transitory computer-readable medium according to claim 10, wherein the method further comprising estimating a position of an insertion point of the endoscope into a body of patient based on the first result or the second result.

12. The non-transitory computer-readable medium according to claim 10, wherein the method comprising:
extracting coordinates of corresponding points by associating the first feature points with the second feature points; and
estimating the first result based on the coordinates of the corresponding points.

13. The non-transitory computer-readable medium according to claim 10, wherein the sensor is attached to at least one of the endoscope and a trocar.

* * * * *